United States Patent [19]

Crutchfield et al.

[11] 4,182,900
[45] Jan. 8, 1980

[54] ETHER DICARBOXYLATES

[75] Inventors: Marvin M. Crutchfield, Creve Coeur; Victor D. Papanu, Maryland Heights; Charles J. Upton, Ballwin, all of Mo.

[73] Assignee: Monsanto Company, St. Louis, Mo.

[21] Appl. No.: 945,973

[22] Filed: Sep. 26, 1978

[51] Int. Cl.² ............................................. C07C 59/22
[52] U.S. Cl. ................................... 560/180; 562/583; 252/132; 252/180; 252/DIG. 11; 260/501.17
[58] Field of Search .................... 560/180; 562/583; 260/501.17

[56] References Cited

U.S. PATENT DOCUMENTS

| | | | |
|---|---|---|---|
| 3,911,003 | 10/1975 | Suzuki | 560/180 |
| 4,025,450 | 5/1977 | Lamberti | 562/583 |
| 4,100,358 | 7/1978 | Lannert | 252/89 R |

OTHER PUBLICATIONS

Kirk-Othmer "Encyclopedia of Chemical Technology," vol. 1, (1947), 1st Ed., pp. 43-45, Acetals.
Arbuzov, Yu A et al., Chemical Abstracts 58 #12416 (de).
Interchemical Corporation, (Brit. 1,092,615), Chemical Abstracts 69, (1968), #2516w.

*Primary Examiner*—Bernard Helfin
*Assistant Examiner*—L. Hendriksen
*Attorney, Agent, or Firm*—S. M. Tarter; E. P. Grattan; F. D. Shearin

[57] ABSTRACT

Ether carboxylates represented by the formula:

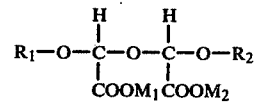

wherein $R_1$ and $R_2$ are individually selected from the group consisting of alkyl containing up to 20 carbon atoms and $M_1$ and $M_2$ are individually selected from the group consisting of alkyl containing up to about 4 carbon atoms, are useful as intermediates to prepare the corresponding acid or alkali metal, ammonium and alkanol amine salts, which are useful as chelants, sequestrants and detergent builders.

10 Claims, No Drawings

ETHER DICARBOXYLATES

BACKGROUND OF THE INVENTION

This invention relates to ether carboxylates useful as chelants, sequestrants and detergent builders.

The property possessed by some materials of improving detergency levels of soaps and synthetic detergents and the use of such materials in detergent compositions is known. Such cleaning boosters are called "builders" and such builders permit the attainment of better cleaning performance than is possible when so-called unbuilt compositions are used. The behavior and mechanisms by which builders perform their function are only partially understood. It is known that good builders must be able to sequester most of the calcium and/or magnesium ions in the wash water since these ions are detrimental to the detergency process. However, it is difficult to predict which class of compounds possess useful combinations of builder properties and which compounds do not because of the complex nature of detergency and the countless factors which contribute both to overall performance results and the requirements of environmental acceptability.

Sodium tripolyphosphate (STP) has been found to be a highly efficient cleaning and detergent builder and this compound has been widely used for decades in cleaning and detergent formulations. Indeed, millions of pounds of STP are used each year in cleansing formulations because of its superior builder qualities. However, because of the recent emphasis on removing phosphates from detergent and cleaning compositions for environmental reasons, the detergent and cleaning industry is now looking for materials suitable for use as builders which do not contain phosphorus, and which are environmentally acceptable.

A large number of materials which do not contain phosphorus have been evaluated for use in detergent and cleaning formulations as a builder, and some of these materials have been ether carboxylates. As an example, U.S. Pat. Nos. 3,865,755 and 4,100,358 disclose the use of ether polycarboxylates as chelants, sequestrants and detergent builders. In addition, applications Ser. No. 826,424, Ser. No. 826,425 and Ser. No. 826,426 all filed on Aug. 22, 1977 relate to polyacetal carboxylates and methods for making and using such carboxylates.

Although satisfactory results are achieved using the polycarboxylates set forth above, there remains a need for new and structurally different polycarboxylates to satisfy specialized applications in detergent formulations. Hence, those skilled in the art of detergent formulation are constantly looking for polycarboxylates for use as chelants, sequestrants and detergency builders in such formulations, and the present invention provides to the art a class of polycarboxylates that are structurally different from the prior art suitable for use in such applications.

SUMMARY OF THE INVENTION

These advantages are achieved by a compound represented by the formula:

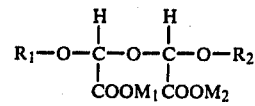

wherein $R_1$ and $R_2$ are individually selected from the group consisting of alkyl containing up to 20 carbon atoms, and $M_1$ and $M_2$ are individually selected from the group consisting of hydrogen, alkali metal, ammonium, alkanol amine containing up to about 4 carbon atoms, and alkyl containing up to about 4 carbon atoms.

Broadly described, the compounds of the present invention can be prepared by forming an alkali metal alkoxide from an alkali metal alcoholate and a dialkyl ketomalonate to form an intermediate alkali metal alkoxide and bringing together under reaction conditions the alkali metal alkoxide with an alkyl haloalkoxy acetate to provide an ether tricarboxylate. The ether tricarboxylate is then converted to the ester form of the dicarboxylate compound of the present invention by decarboxylation with an alkali metal halide in a suitable solvent such as dimethyl sulfoxide. The ester can then be saponified by conventional techniques to form the salt form of the present invention. The acid form of the compound of the present invention can be formed from the salt by acidulation with a suitable acid.

Any number of alkali metal alcoholates known to those skilled in the art can be used in the process to prepare the compounds of the present invention. The alkali metal alcoholates can be prepared by known methods such as the reaction of an alkali metal hydride, such as lithium hydride, sodium hydride or potassium hydride, with an alcohol. The alcohols can contain from 1 to about 20 carbon atoms or even more carbon atoms, although the presence of additional carbon atoms is not advantageous. Suitable alcohols for preparing the alkali metal alcoholate useful as an intermediate to prepare the compound of the present invention for use as a builder include methanol, ethanol, isopropanol, propanol, isobutanol, butanol and the like. Sodium alcoholates containing 1 to 4 carbon atoms are preferred and sodium methoxide is especially preferred.

On the other hand, suitable alcohols for preparing the alkali metal alcoholate useful as an intermediate to prepare the compounds of the present invention for use as a builder with surfactant and emulsification properties include alcohols having about 10 to about 20 carbon atoms. Such alcohols can be branched or straight chain aliphatics, and can be substituted with other groups like nitro, cyano, benzyl and/or alkylbenzyl provided that such groups do not interfere with the use of the alcoholate as an intermediate to prepare the compounds of the present invention. Aromatic alcohols such as phenol and alkyl-substituted phenol can also be used. It is preferred to use an aliphatic alcohol containing from about 12 to about 16 carbon atoms, such as dodecanol, to prepare the compound of the present invention with builder and surfactant or emulsification properties.

Any number of dialkyl ketomalonates known to those skilled in the art can be used in the process to prepare the compounds of the present invention. It is only necessary that the alkyl groups on the ketomalonate do not interfere in the reaction with the alkali metal alcoholate to form the sodium alkoxide, or interfere with the subsequent reaction of the sodium alkoxide with the alkyl haloalkoxyacetate to form the intermediate to the compound of the present invention. Hence, the dialkyl groups can contain any number of carbon atoms, but it has been found that alkyl groups containing from 1 to about 4 carbon atoms provide satisfactory results. The alkyl groups on the dialkyl ketomalonates can be alike or unlike and suitable dialkyl ketomalonates include dimethyl ketomalonate, methylethyl ketomalonate, diethyl ketomalonate, methylpropyl ketomalonate, ethylpropyl ketomalonate, dipropyl ketomalonate, methylisopropyl ketomalonate, ethylisopropyl ketomalonate, propyl isopropyl ketomalonate, dibutyl ketomalonate, diisobutyl ketomalonate, methylisobutyl ketomalonate, ethylbutyl ketomalonate, isopropylbutyl ketomalonate, and the like. Dimethyl ketomalonate, diethyl ketomalonate and methylethyl ketomalonate are preferred.

The alkyl haloalkoxyacetates suitable for use to prepare the compounds of the present invention are known to those skilled in the art. It is only necessary that the alkyl haloalkoxyacetate react with the alkali metal alkoxide intermediate to form the compound of the present invention. Suitable alkyl haloalkoxyacetates include the chloro, bromo and iodo derivatives of alkyl methoxyacetate, ethoxyacetate, propoxyacetate, isopropoxyacetate, butoxyacetate and isobutoxyacetate. The alkoxy moiety in the haloalkoxyacetate can contain from 1 to 20 carbon atoms, or even more carbon atoms, but there does not seem to be a particular advantage of having more than 20 carbon atoms. To prepare the compound of the present invention useful as a builder it is preferred that the alkoxy moiety contain from 1 to about 4 carbon atoms, such as methoxy, ethoxy, butoxy, isopropoxy, isobutoxy and the like. To prepare the compound of the present invention having surfactant and emulsifier properties in addition to builder properties, it is preferred that the alkoxy moiety contain from about 10 to about 20 carbon atoms. Such alkoxy moieties can be branched or straight chain aliphatics, and can be substituted with other groups like nitro, cyano or aromatic groups. It is preferred to use an alkoxy containing from 12 to 16 carbon atoms. An alkyl halomethoxyacetate is preferred and alkyl bromomethoxyacetate is particularly preferred.

In order to form the alkali metal alkoxide, it is only necessary to bring together the alkali metal alcoholate and the dialkyl ketomalonate in the presence of a solvent, such as tetrahydrofuran, at a temperature between about 0° and about 25° C. and at atmospheric pressure. The exact conditions of the reaction can be readily determined by those skilled in the art who may desire to run the reaction at higher or lower pressures or at higher or lower temperatures. However, satisfactory results have been obtained by bringing the sodium alcoholate and the dialkyl ketomalonate together in a tetrahydrofuran solvent at atmospheric pressure and at a temperature of from about 0° to about 10° C.

In order to form the intermediate to the compound of the present invention it is only necessary to bring together the alkali metal alkoxide prepared as described above with the alkyl haloalkoxyacetate, preferably in the presence of a solvent such as tetrahydrofuran. Satisfactory results have been achieved by bringing together the alkali metal alkoxide and the alkyl haloalkoxyacetate at normal atmospheric pressure, although higher or lower pressures may be used. The temperature of the reaction can be conducted at temperatures between 0° C. and about 25° C., although the conditions of temperature and pressure may be readily determined by those skilled in the art without undue experimentation. For example, when alkyl bromomethoxyacetate is reacted with a sodium alkoxide intermediate to form the tricarboxylate intermediate, satisfactory results are achieved at atmospheric pressure and at temperatures between about 10° C. and about 25° C. However, as is known to those skilled in the art, higher temperatures may be required if an alkyl chloroalkoxyacetate is used in lieu of the alkyl bromoalkoxyacetate.

The tricarboxylate prepared above can be decarboxylated in accordance with procedures known to those skilled in the art. The general procedure of A. P. Krapcho and A. J. Lovey, TETRAHEDRON LETTERS, page 957 (1973), was found to provide satisfactory results by treating the tricarboxylate with an alkali metal halide, such as sodium chloride, in the presence of a suitable solvent, such as tetrahydrofuran, at a temperature between about 120° C. and 200° C., preferably between 150° C. and 170° C.

As will occur to those skilled in the art in light of the present disclosure, the number of carbon atoms in the alkoxy moiety and the alcoholate determine the number of carbon atoms in $R_1$ and $R_2$ in the formula of the compound of the present invention:

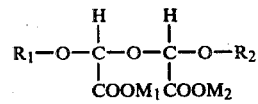

When the combined number of carbon atoms in $R_1$ and $R_2$ is less than about 10, preferably less than about 6, the compound is particularly useful as a chelant, sequestrant and detergent builder. However, when the compound of the present invention is to be used as a surfactant or emulsifier in addition to its chelation, sequestration or builder properties, the combined number of carbon atoms in $R_1$ and $R_2$ should be in the range of about 10 to about 24, preferably between about 13 and about 18. In the latter case it is particularly advantageous when $R_1$ contains from about 12 to about 16 carbon atoms and $R_2$ is methyl or ethyl.

On the other hand, the ether dicarboxylate ester of the present invention can be prepared, although in lower yields, by bringing together the glyoxylate hemiacetal with glyoxylate followed by treatment with a dialkyl sulfate according to the following general equation:

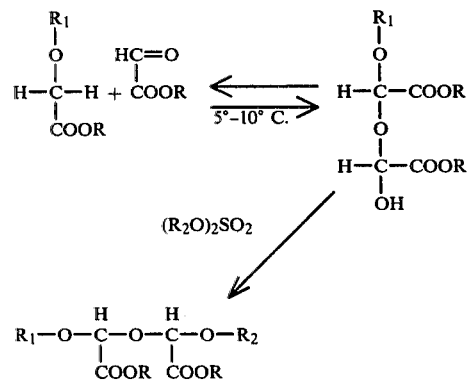

wherein each R individually is an alkyl of 1 to 4 carbon atoms, and $R_1$ and $R_2$ are as defined above.

The ester form of the compound of the present invention is useful as an intermediate to prepare the corresponding alkali metal, ammonium or alkanol amine salts or the acid form by conventional techniques, and the acid and salt forms are useful as agents for complexing metals and/or alkaline earth ions in aqueous media. The alkali metal salt of the compound of the present invention can be prepared by converting the ester form of the compound to the alkali metal salt by conventional saponification techniques. As will occur to those skilled in the art in view of the present disclosure, the ester can be partially saponified to produce a mixed ester and salt. On the other hand, the salt form of the compounds of the present invention can be neutralized with an acid by acidulation to pH 2 to form the corresponding acid form. As will occur to those skilled in the art in view of the present disclosure, partial neutralization will produce a mixture of the acid and ester forms or a mixture of the salt and acid form to provide a compound with specialized characteristics, such as a different crystallinity, lowered hydroscopicity and the like.

The amount of the acid or salt form required to effectively complex the ions in a given system will depend to some extent on the particular compound being used and the particular metal or alkaline earth metal ion in the aqueous media. Optimum conditions and amounts of the compound of the present invention to be used can be readily determined by routine experimentation.

The salt forms of the compounds of the present invention are useful as builders in detergent formulations. Generally, the use of the alkali metal salts, particularly the sodium salt, is preferred. However, in some formulations where greater builder solubility is required, the use of ammonium or alkanol amine salts may be desirable and such salts can be readily prepared from the alkali metal salts by conventional ion exchange techniques. The alkanol amine salts may be preferred in some formulations, such as liquid formulations where greater builder solubility is required, and the alkanol amine moiety may contain from 1 to 20 carbon atoms in the alkyl chain, preferably 1 to 4 carbon atoms.

Detergent formulations will normally contain at least 1 percent by weight and preferably at least 5 percent by weight of the salt compounds of the present invention. In order to obtain the maximum advantages of the salt compounds of the present invention, the use of from about 5 percent to about 75 percent of the salt compound is preferred. The salt compounds of the present invention can be utilized in combination with other detergency builders which may constitute from 0 to 95 percent by weight of the total builders in the formulation. By way of example only, builders which can be employed in combination with the salt compounds of the present invention include water soluble inorganic builder salts, such as alkali metal polyphosphates, i.e., trisodium polyphosphate and sodium pyrophosphate, alkali metal carbonates, borates, bicarbonates, silicates and water soluble organic builders including amino polycarboxylic acids and salts such as alkali metal nitrilotriacetate, cycloalkane polycarboxylic acids and salts, ether polycarboxylates, alkyl polycarboxylates, epoxy polycarboxylates, tetrahydrofuran polycarboxylates, oxidized starches, amino trimethylene phosphonic acid and its salts, diphosphonic acid and its salts, and the like. The total amount of builder employed will be dependent upon the intended use of the detergent formulation, other ingredients of the formulation, pH conditions and the like. For example, general laundry powder formulations will usually contain 20 percent to 60 percent builder, whereas liquid dishwashing formulations will contain from 11 to 12 percent builder. Machine dishwashing formulations will contain from 60 to 90 percent builder. Optimum levels of builder content as well as optimum mixtures of builders of this invention with other builders for various uses can be determined by routine tests in accordance with conventional detergent formulation practice.

Any water soluble anionic, nonionic, zwitterionic or amphoteric surfactant can be employed. The quantity of surfactant employed will depend on the surfactant chosen and the end use of the formulation. Generally, laundry formulations will contain from 5 to 50 percent surfactant by weight, although as much as 95 percent or more surfactant may be employed if desired. For example, general laundry powder formulations normally contain from 5 percent to 50 percent, preferably 15 percent to 25 percent surfactant. Machine dishwashing formulations generally contain up to 5 percent surfactant. Liquid dishwashing formulations will contain from about 20 percent to about 45 percent. It will be understood that the choice and use of surfactants will be in accordance with well understood practices in detergent formulation.

DETAILED DESCRIPTION OF THE INVENTION

The invention is further illustrated by but not limited to the following examples wherein all parts are by weight unless otherwise indicated.

EXAMPLE I

To a 100 milliliter 3-necked round bottomed flask equipped with a nitrogen inlet, an addition funnel, a condenser and an efficient stirrer, 2.1 grams of 50 percent sodium hydride were added. The hydride was washed with three 10 milliliter portions of pentane. The hydride was then suspended in 10 milliliters of tetrahydrofuran. Then, 1.70 milliliters of methanol in 5 milliliters of tetrahydrofuran were added dropwise over a 15-minute period. The resulting slurry of sodium methoxide was stirred 0.5 hour at room temperature, then cooled in an ice bath. Then, 5.6 grams of dimethyl ketomalonate in 5 milliliters of tetrahydrofuran were added dropwise over a 15-minute period. The color of the slurry turned to a pale brownish-green and was stirred one hour at about 10° C. Thereafter, 7.0 grams of methyl methoxybromoacetate in 5 milliliters of tetrahydrofuran were added over a 15-minute period. The mixture quickly turned to a nearly white slurry, and was stirred overnight under a nitrogen atmosphere at room temperature.

The following morning 50 milliliters of water were added, and the mixture was extracted with 100 milliliter portions of diethyl ether and then three times with 50 milliliter portions of diethyl ether. The ether extracts were combined, and washed with a 75 milliliter portion of saturated sodium chloride solution. The ether extracts were dried over magnesium sulfate. The ether was removed using a rotary evaporator to provide about 8.5 grams of a nearly colorless viscous liquid. Analysis by Proton Magnetic Resonance (PMR) revealed that the liquid was primarily the trimethyl ester of 2,4,6-trioxaheptane-3,3,5-tricarboxylate. The ester was purified by vacuum distillation yielding 5.8 grams of clear colorless liquid boiling 122°–128° C. at a pressure of 0.04–0.06 mm Hg.

Then, 5.0 grams (17.8 mmol) of the trioxaheptane tricarboxylate prepared above was dissolved in 14.5 milliliters of dimethyl sulfoxide containing 0.65 gram (36.1 mmol) water and 1.05 grams (18 mmol) sodium chloride. The mixture was heated in an oil bath at 130° C. for 2.5 hours, then for 1 hour at 160° C. at which point the reaction was determined to be complete by gas chromatography. The reaction mixture was cooled, diluted with 25 milliliters of water, and extracted with four 25-milliliter portions of methylene chloride. The methylene chloride extract was washed three times with water, once with saturated sodium chloride solution, and dried over magnesium sulfate. The extract was then concentrated on a rotary evaporator and then vacuum distilled, yielding 2.6 grams (66 percent yield) of dimethyl 2,4,6-trioxaheptane-3,5-dicarboxylate. Purity and structure were determined by gas/liquid chromatography and Proton Magnetic Resonance spectroscopy.

The above ester was hydrolyzed with 10 milliliters of 2.5 molar sodium hydroxide solution at room temperature overnight. Addition of 100 milliliters of methanol precipitated the disodium 2,4,6-trioxaheptane-3,5-dicarboxylate which, after filtration and vacuum drying, weighed 2.6 grams. The overall yield was 36 percent, based on dimethyl ketomalonate.

EXAMPLE II

The disodium-2,4,6-trioxaheptane-3,5-dicarboxylate from Example I was tested for sequestration function using the procedure described by Matzner et al ("Organic Builder Salts as Replacements for Sodium Tripolyphosphate", TENSIDE DETERGENTS, 10, No. 3, pages 119–125 (1973)). The sequestration of calcium ions and magnesium ions (as a percent of STP performance) showed that the trisodium salt had a sequestration performance of about 50 percent of STP.

EXAMPLE III

The compound of the present invention was prepared by reacting 0.1 mole of methyl glyoxylate methyl hemiacetal with methyl glyoxylate at about 7° C. in the presence of para-toluenesulfonic acid. Then, after the reaction mixture had come to equilibrium (about 45 minutes), 0.25 mole dimethyl sulfate and 0.25 mole potassium carbonate were added to the reaction mixture which was then heated to 20° C. The mixture was stirred for about 1 hour, 50 milliliters of water were added, and the mixture was extracted with three 100 milliliter portions of diethyl ether. The ether extracts were combined, backwashed with saturated sodium chloride solution and dried over magnesium sulfate. The ether was removed using a rotary evaporator to provide a nearly colorless viscous liquid, which had a boiling point between 92° and 98° C. at 0.03 millimeters Hg. Analysis confirmed the presence of the dimethyl ester of 2,4,6-trioxaheptane-3,5-dicarboxylate.

The ester was hydrolyzed to the corresponding salt using 5 grams of 50 percent aqueous sodium hydroxide solution at room temperature according to the general procedure set forth in Example I. The overall yield was about 10 percent, based on the moles of methyl glyoxylate methyl hemiacetal.

EXAMPLE IV

The general preparative procedure of Example I is repeated using an equivalent amount of dodecanol instead of methanol to form the sodium alkoxide. The resulting product from the procedure after hydrolysis

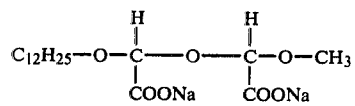

has surfactant and emulsification properties in addition to its ability to sequester calcium and magnesium ions.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A compound represented by the formula:

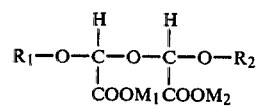

where $R_1$ and $R_2$ are individually selected from the group consisting of alkyl containing up to about 20 carbon atoms, and $M_1$ and $M_2$ are individually selected from the group consisting of hydrogen, alkali metal, ammonium, alkanol amine containing up to about 4 carbon atoms, and alkyl containing up to about 4 carbon atoms.

2. A compound of claim 1 wherein $R_1$ and $R_2$ individually contain 1 to about 4 carbon atoms.

3. A compound of claim 1 wherein $R_1$ contains about 10 to about 20 carbon atoms.

4. A compound of claim 1 wherein $R_1$ contains about 12 to about 16 carbon atoms.

5. A compound of claim 4 wherein $R_2$ contains 1 to about 4 carbon atoms.

6. A compound of claim 1 wherein $R_1$ and $R_2$ are each methyl.

7. A compound of claim 1 wherein $M_1$ and $M_2$ are alkali metal.

8. A compound of claim 1 wherein $M_1$ and $M_2$ are alkyl containing up to about 4 carbon atoms.

9. A compound of claim 2 wherein $M_1$ and $M_2$ are alkali metal.

10. A compound of claim 5 wherein $M_1$ and $M_2$ are sodium.

* * * * *